(12) United States Patent
Breindel et al.

(10) Patent No.: US 11,565,087 B2
(45) Date of Patent: Jan. 31, 2023

(54) BLOOD CONTAINMENT FOR IV CATHETER

(71) Applicant: SMITHS MEDICAL ASD, INC., Plymouth, MN (US)

(72) Inventors: Jay T Breindel, Southington, CT (US); David J Goral, Brookfield, CT (US); Christopher Roehl, New Hartford, CT (US)

(73) Assignee: Smiths Medical ASD, Inc, Plymouth, MN (US)

(*) Notice: Subject to any disclaimer, the term of this patent is extended or adjusted under 35 U.S.C. 154(b) by 359 days.

(21) Appl. No.: 16/065,608

(22) PCT Filed: Mar. 6, 2018

(86) PCT No.: PCT/US2018/021155
§ 371 (c)(1),
(2) Date: Jun. 22, 2018

(87) PCT Pub. No.: WO2018/165166
PCT Pub. Date: Sep. 13, 2018

(65) Prior Publication Data
US 2019/0388653 A1 Dec. 26, 2019

Related U.S. Application Data

(60) Provisional application No. 62/485,146, filed on Apr. 13, 2017, provisional application No. 62/467,397, filed on Mar. 6, 2017.

(51) Int. Cl.
*A61M 25/06* (2006.01)
*A61M 25/00* (2006.01)

(52) U.S. Cl.
CPC .... *A61M 25/0606* (2013.01); *A61M 25/0097* (2013.01); *A61M 25/0693* (2013.01); *A61M 25/0618* (2013.01)

(58) Field of Classification Search
CPC ............ A61M 5/3273; A61M 25/0693; A61M 25/0631; A61M 25/0618; A61M 25/0606;
(Continued)

(56) References Cited

U.S. PATENT DOCUMENTS

| 4,755,356 A | 7/1988 | Robbins et al. |
| 5,697,914 A | 12/1997 | Brimhall |

(Continued)

FOREIGN PATENT DOCUMENTS

| SG | 173383 A1 | 8/2011 |
| WO | 2002096495 A2 | 12/2002 |

(Continued)

OTHER PUBLICATIONS

International Search Report and Written Opinion, dated May 16, 2018 in PCT/US2018/021135.
(Continued)

*Primary Examiner* — Tiffany Legette
(74) *Attorney, Agent, or Firm* — Louis Woo (57) ABSTRACT

Catheter assemblies may include introducer needles having a notch or similar structure that allows flashback blood to enter the annular space between a catheter tube and an introducer needle of an IV catheter. The presence of flashback blood in this annular space can provide a clinician with an early, visible indication that a needle has entered a vein. The notch, however, may create a leak path for blood to escape outside of the catheter assembly, unless contained. Disclosed herein is a notch containment that prevents the notch from providing a leak path for blood to escape outside of the catheter during or after needle withdrawal.

18 Claims, 6 Drawing Sheets

(58) Field of Classification Search
CPC .............. A61M 39/06; A61M 39/0606; A61M 39/045; A61M 2039/066; A61M 2039/0633; A61M 25/0097; A61M 25/0612; A61M 25/0625; A61M 25/028; A61M 25/0286; A61M 2039/062
See application file for complete search history.

(56) References Cited

U.S. PATENT DOCUMENTS

| | | | |
|---|---|---|---|
| 5,810,780 A * | 9/1998 | Brimhall | A61M 25/0693 604/167.02 |
| 6,497,994 B1 | 12/2002 | Kafrawy | |
| 7,736,337 B2 | 6/2010 | Diep et al. | |
| 8,979,803 B2 | 3/2015 | Darr et al. | |
| 2003/0105431 A1 | 6/2003 | Howell | |
| 2004/0267200 A1 | 12/2004 | Carylon et al. | |
| 2005/0015071 A1 | 1/2005 | Brimhall | |
| 2008/0097344 A1* | 4/2008 | McKinnon | A61M 25/0637 604/263 |
| 2008/0300543 A1 | 12/2008 | Abriles et al. | |
| 2010/0222746 A1 | 9/2010 | Burkholz | |
| 2011/0288482 A1 | 11/2011 | Farrell et al. | |
| 2012/0065612 A1 | 3/2012 | Stout et al. | |
| 2012/0136311 A1 | 5/2012 | Knutsson et al. | |
| 2012/0232499 A1* | 9/2012 | Stout | A61M 39/06 604/256 |
| 2012/0323181 A1 | 12/2012 | Shaw et al. | |
| 2014/0364809 A1* | 12/2014 | Isaacson | A61M 25/0009 604/164.08 |
| 2015/0151084 A1* | 6/2015 | Teoh | A61M 25/0606 604/510 |
| 2016/0106959 A1 | 4/2016 | Woehr | |

FOREIGN PATENT DOCUMENTS

| | | |
|---|---|---|
| WO | 2004032995 A2 | 4/2004 |
| WO | 2015024904 A1 | 2/2005 |
| WO | 2007050788 A2 | 5/2007 |
| WO | 2016526395 A | 9/2016 |
| WO | 2017074677 A1 | 5/2017 |

OTHER PUBLICATIONS

International Search Report and Written Opinion, dated May 11, 2018, in PCT Application No. PCT/US2018/21143.
International Search Report and Written Opinion of the International Searching Authority, dated Apr. 27, 2018 in PCT Application No. PCT/US2018/21155.
Supplementary EP Search Report for EP Application No. 18763445.6, dated Jan. 8, 2020.
AUIPO Examination Report dated Oct. 10, 2019 in Application No. 2018231164.
CIPO Notice of Allowance dated Dec. 10, 2019 in Application No. 3053800.
Office Action for JP Application No. 2019-546899, dated Jan. 8, 2020.
Office Action for AU Application No. 2018231164, dated Jun. 2, 2020.

* cited by examiner

BLOOD CONTAINMENT FOR IV CATHETER

CROSS-REFERENCE TO RELATED APPLICATIONS

This application is U.S. national phase filing under 35 U.S.C. § 371 of PCT/US2018/21155 (the "155 application") filed on Mar. 6, 2018 and entitled "BLOOD CONTAINMENT FOR IV CATHETER." The '155 application claims priority from U.S. Ser. No. 62/467,397 filed on Mar. 6, 2017 and entitled "PERIPHERAL IV CATHETER," and U.S. Ser. No. 62/485,146, filed on Apr. 13, 2017 and entitled "BLOOD CONTAINMENT FOR IV CATHETER." All of the aforementioned applications are incorporated herein by reference in their entirety for all purposes.

FIELD

The present disclosure relates to intravenous (IV) catheters and more particularly to IV catheters that include features to provide an early indication of needle or catheter entry into a vein.

RELATED ART

Safety catheter assemblies typically include a catheter and a catheter introducer having an insertion needle. The catheter is provided assembled to the introducer in a ready for use configuration with a tube of the catheter positioned over the insertion needle and a sharp tip of the insertion needle protruding from a distal end of the catheter. A needle sheath may be positioned over the sharp tip of the insertion needed to prevent unwanted needle sticks prior to the catheter assembly being used. The overall safety catheter assembly, including the catheter, catheter introducer, and needle sheath, may be provided for use in a sterilized and assembled state, contained within a sealed package. One example of such a safety catheter includes the JELCO INTUITIV (Trademark) safety catheter marketed by Smiths Medical ASD, Inc. of Plymouth, Minn., as described in U.S. Pat. No. 8,257,322.

To insert the catheter into the vein of a subject, a clinician first removes the safety catheter assembly from the packaging. The needle sheath is removed to expose the sharp tip of the insertion needle that is protruding from the distal end of the catheter. The clinician punctures an identified site of a subject with the sharp needle tip and urges the insertion needle forward until the needle tip enters the vein of the subject. An initial amount of blood may pass through a lumen of the needle, entering the catheter and/or catheter introducer where the clinician may view the "flashback" of the blood to confirm entry into the vein. The catheter may then be moved distally over the needle to thread the tube of the catheter into position in the vein of the subject. With the catheter positioned as desired, the clinician withdraws the needle by pulling the catheter introducer proximally away from the subject while holding the catheter generally stationary with respect to the subject until the needle and introducer are separated from the catheter. Safety features may be actuated, passively or actively, during needle withdrawal to prevent access to the sharp needle tip once withdrawn from the catheter. The clinician may dispose of the catheter insertion device in a sharps container, after the insertion device is separated from the catheter.

Some catheter assembly include a needle having a notch or window on a lateral side of needle, proximal to the distal end of the needle. The notch is positioned in the catheter tube when the catheter assembly is in the ready for use position. When a clinician introduces the needle tip into the vein of a subject, flashback blood passes up the needle lumen, out of the notch and into the annular space between the catheter and needle. The presence of flashback blood in this space can provide the clinician with a desirable, early, visible indication of entry into the vein of a subject.

BRIEF DESCRIPTION OF THE FIGURES

In the drawings, different embodiments of the invention are illustrated in which.

DETAILED DESCRIPTION

Catheter assemblies may include introducer needles having a notch or similar structure that allows flashback blood to enter the annular space between a catheter tube and an introducer needle of an IV catheter. The presence of flashback blood in this annular space can provide a clinician with an early, visible indication that a needle has entered a vein. The notch, however, may create a leak path for blood to escape outside of the catheter assembly, unless contained.

Disclosed herein is a notch containment that prevents the notch from providing a leak path for blood to escape outside of the catheter during or after needle withdrawal. This may otherwise occur, according to some catheter assemblies, when a distal end of the introducer needle is in fluid communication with blood that lies within a catheter while the notch is outside of the catheter. To prevent the escape or egress of blood through the notch, catheter assemblies include a containment that is positioned at least partially proximal to and external of the catheter hub and that receives the notch as the needle is withdrawn. The containment may separate from the catheter as the introducer separates from the catheter.

Figure 1A:
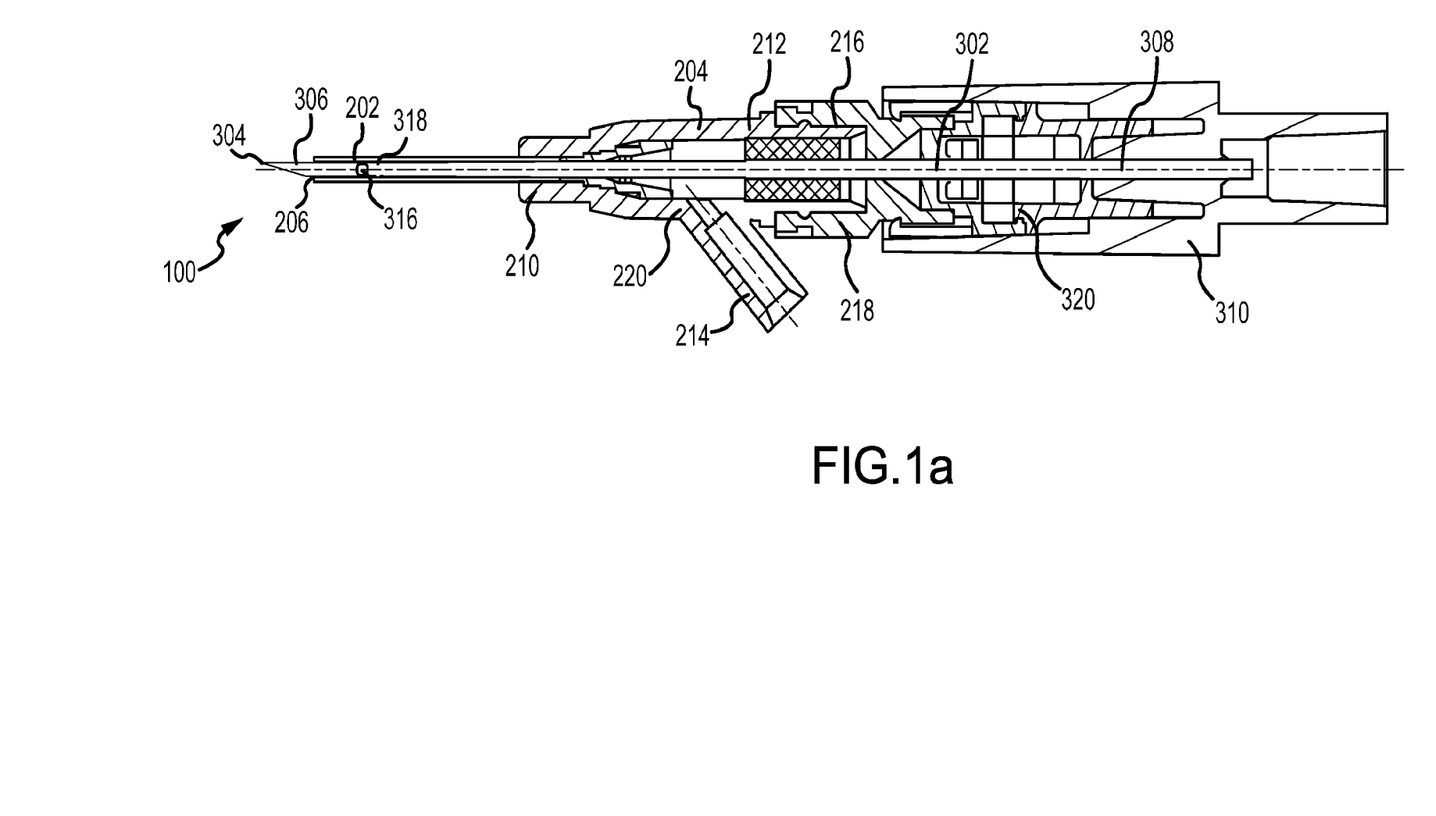
FIG. 1a is a partial, cross sectional view of an intravenous catheter assembly having a notch in the introducer needle and configured in a ready position, according to one example embodiment.
Figure 1B:
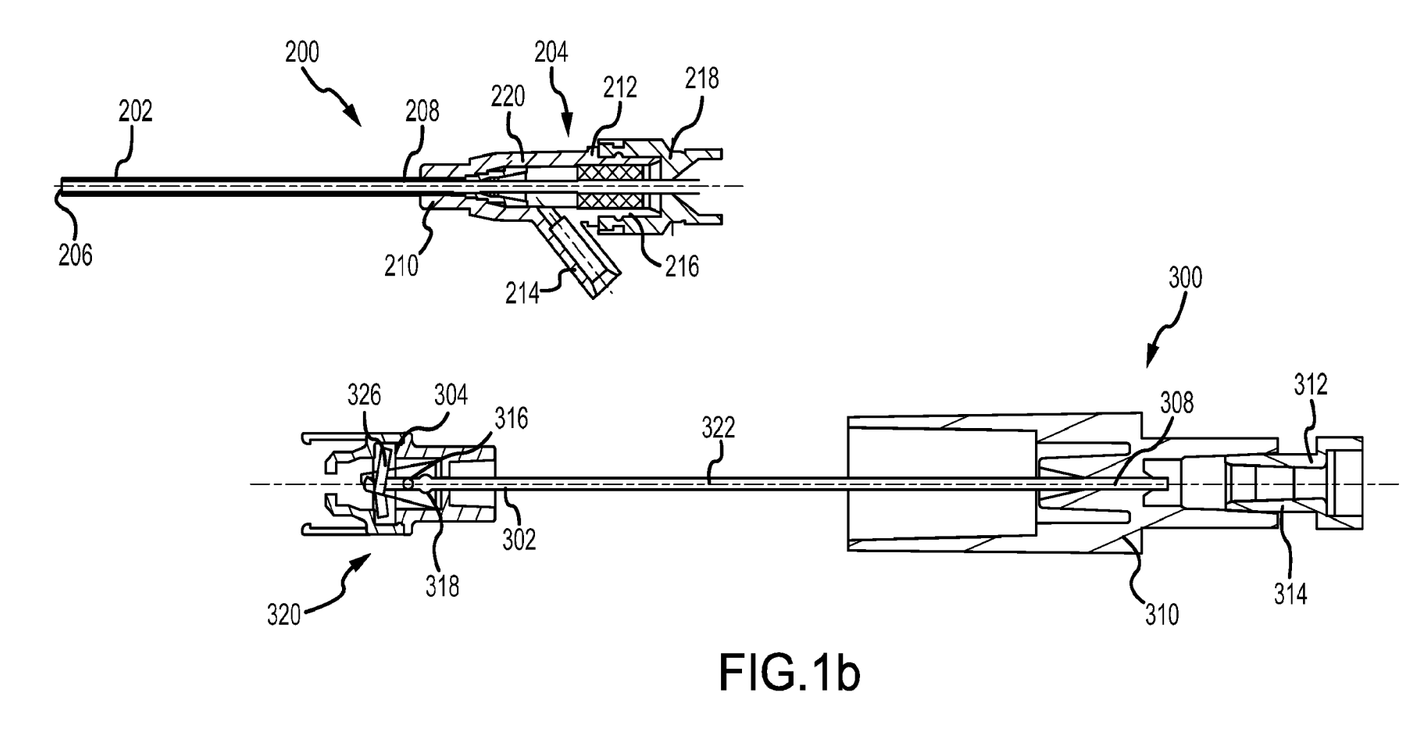
FIG. 1b is a partial, cross sectional view of the intravenous catheter assembly of FIG. 1a, configured in a safe position.

Turn now to the figures, and initially FIGS. 1a and 1b that show an example embodiment of a catheter assembly 100 that includes a catheter 200 and a catheter introducer 300. FIG. 1a shows the catheter assembly 100 in a ready position, as configured ahead of a clinician initiating a catheter insertion procedure. FIG. 1b shows the catheter assembly 100 in a safe position with the catheter 200 separated from the catheter introducer 300 and access to the sharp tip of the introducer needle prevented by a safety device.

The catheter 200 includes a catheter tube 202, a catheter hub 204, and an extension tube (not shown) that cooperate to provide a fluid pathway between the vein of a subject and other IV fluid components, such as an IV fluid supply. The catheter tube 202 includes a distal end 206, a proximal end 208, and a lumen extending therebetween. The catheter hub 204 includes a distal end 210, a proximal end 212 and a side port 214, in the illustrated example embodiment. The proximal end 212 of the catheter tube 202 is connected to a distal portion 210 of the catheter hub. The side port 214 is connected to the extension tube, thereby providing fluid communication from the extension tube, through the catheter hub and into the catheter tube. The proximal end of the catheter hub 212 houses an elastomeric septum 216 that is secured to the catheter hub by a septum retainer 218. The septum 216 both provides an access pathway for the insertion needle into the catheter tube and seals the interior of the catheter hub to prevent fluid escape from the catheter hub, both while the introducer needle is present and after the introducer needle is removed.

The catheter introducer 300, in the illustrated example embodiment of FIGS. 1a and 1b, includes an insertion needle 302 having a sharp distal tip 304 that is used to create an entry passageway into the vein of a subject. The insertion needle 302 extends from a sharp distal tip at a distal end 306 to a proximal portion 308 that is connected to a needle hub 310 and defines an internal lumen that extends therebetween. A flash plug 312 is connected to the needle hub 310 and may include a microporous barrier 314 that permits the escape of air but prevents the escape of fluid. A notch 316 on a lateral side of the needle 302 provides fluid communication between the lumen and the interior space of a catheter tube 202, when the catheter assembly is in the ready for use position. The body of the insertion needle 302 includes a transition 318 or bump that interacts with the safety device to move the catheter assembly between the ready and the safe positions, according to some example embodiments.

The catheter introducer 300 includes a needle safety device 320 that prevents access to the sharp needle tip 304 after the catheter introducer 300 is separated from the catheter 200. The safety device shown in FIGS. 1a and 1b is a tip protector type device that prevents access to the needle tip without preventing access to the needle body 322. As may be seen in FIG. 1a, the safety device 320 may be positioned adjacent to the catheter hub 204 and about the body of the introducer needle 302 with the catheter assembly 100 is in the ready position. The introducer needle 302 is pulled proximally through the safety device 320 during needle withdrawal until the needle transition 318 engages the tip protector 326, after which the safety device is pulled proximally with the needle and away from the catheter. It is to be appreciated although the example embodiment of FIGS. 1 and 2 utilizes a tip protector as a safety device, that other types of safety devices are also contemplated, including devices that prevent access to a greater proportion or even all of an introducer needle, once in the safe position.

As may be appreciated, the notch 316 of an introducer needle that lacks a containment may provide a leak path for blood to escape the interior of the catheter when the notch of the introducer needle is positioned proximal of the elastomeric septum and outside of the catheter with the tip of the needle exposed to blood under within the catheter. Blood escape may be exacerbated if the distal end of the introducer needle is positioned to blood that is under the pressure from the vascular system of the subject.

Figure 2A:
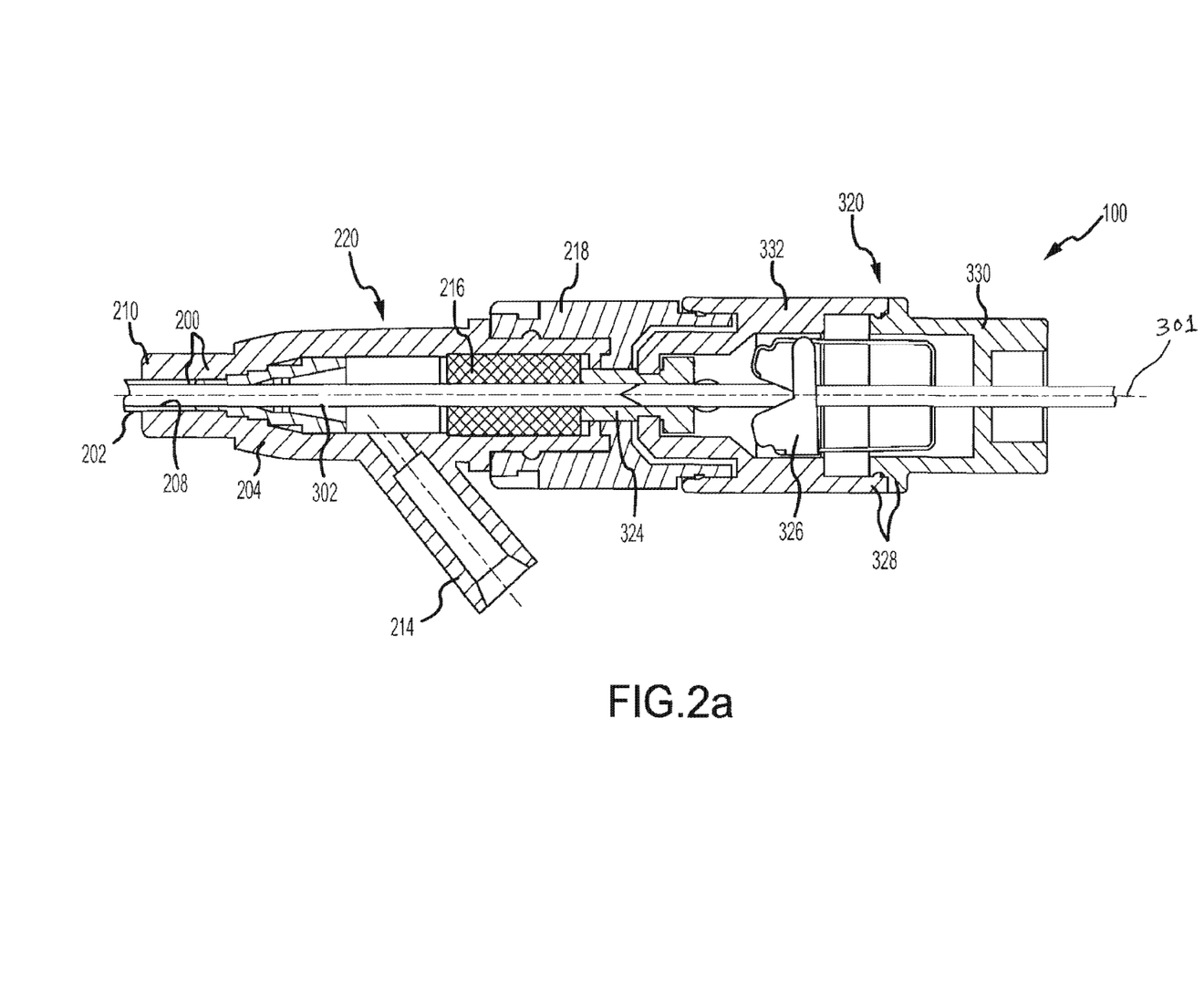
FIG. 2a is a partial, cross sectional view of an intravenous catheter assembly having a notch in the introducer needle and an elastomeric containment according to one example embodiment; the catheter assembly is configured in a ready position.
Figure 2B:
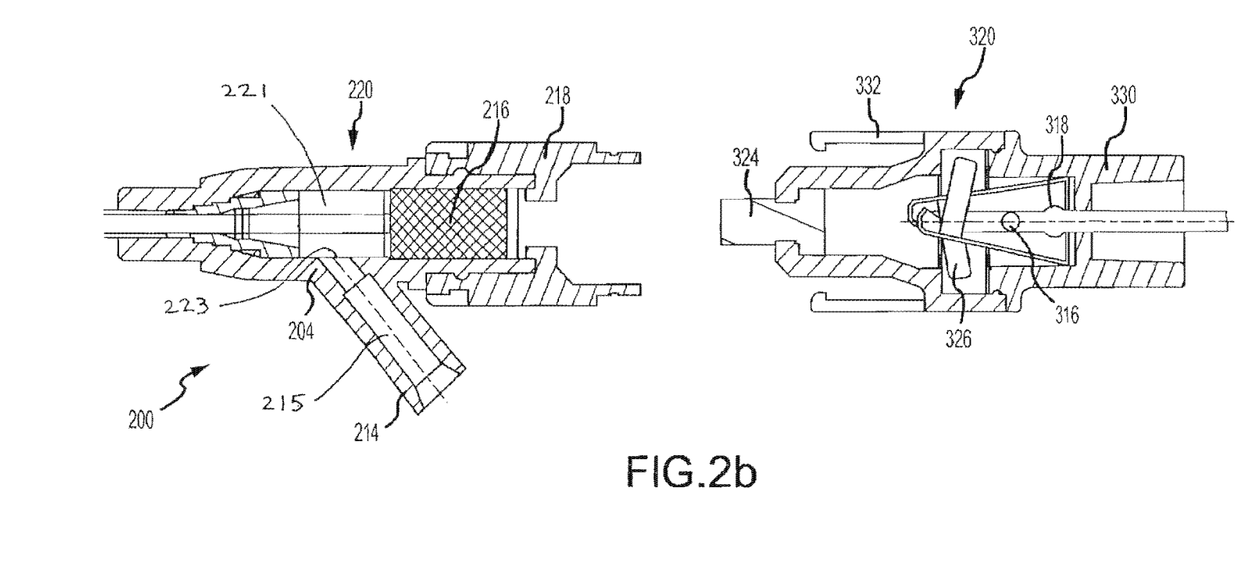
FIG. 2b is a partial, cross sectional view of the intravenous catheter assembly of FIG. 2a, configured in a safe position.

FIGS. 2a and 2b show partial views an example embodiment of a catheter assembly 100 that is equipped with a containment 324 positioned to receive the notch 316 of the introducer needle 302 as the notch 316 emergences from the catheter during needle withdrawal. The catheter assembly 100 is in the ready position in FIG. 2a and the safe position in FIG. 2b. The containment prevents the egress of any blood that might otherwise pass to the environment from the notch. In the example embodiment of FIGS. 2a and 2b, the catheter hub includes a catheter hub body 220 and a septum retainer 218 that is connected to the proximal end of the catheter hub body 220. The internal chamber 221 or simply the interior defined by catheter hub body 220 of catheter hub 204 is in fluid communication with the internal passageway 215 of side port 214 via an opening 223. The safety device 320 includes a spring clip type tip protector 326 and a tip protector housing 328 having a distal housing body 330 and a proximal housing body 332, similar to those shown in FIGS. 1a and 1b and as described in European Patent Application EP 2 204 204, which is hereby incorporated by reference in its entirety.

Containments, according to various example embodiments, may be constructed to conform to an introducer needle. Conformance to the needle may promote sealing of any notch or similar structure to prevent the egress of fluids therefrom. The example embodiment of FIGS. 2a and 2b includes an elastomeric containment 324 that receives and conforms to the outer surface of the needle about the notch 316. Some examples of elastomeric materials include polyisoprene and silicone, to name a few, although other materials area also contemplated.

The containment may be positioned to prevent the egress of fluids from the notch as the notch passes from the septum. By way of example, the containment 324 shown in FIG. 2a abuts the proximal side of the elastomeric septum 216. The notch 316 enters the containment 324 just as the notch emerges from the septum 216. In this respect, any egress of fluid from the notch may be prevented at all points during needle withdrawal from the catheter. It is to be appreciated that this function may be accomplished with different structures, including structures that include containments that engage a catheter hub or septum in manners different than is shown in FIG. 2a. As shown in FIG. 2a, catheter hub 204, containment 324 and needle safety device 320 are in alignment along the longitudinal axis 301. Needle hub 310 is shown in FIGS. 1a-1b to be in axial alignment with catheter hub 204 and needle safety device 320.

The overall length of the septum 216 and the containment 324, as assembled in the ready position, may be longer than the distance between the distal end of the introducer needle and the proximal end of the notch. Constructing the device in this manner may prevent the notch from being exposed to the ambient environment at the same time that the distal end of the needle is exposed to blood of a subject that is under pressure, such as may exist inside of the catheter hub. Such a construction may help prevent the egress of fluids from the notch, thus minimizing risks for blood exposure.

The containment may be held connected to the catheter hub, according to various example embodiments. By way of example, the containment of FIGS. 2a and 2b may be compressed slightly within the aperture of the septum retainer 218 to help hold the containment in position within the catheter hub 204. The interference between the containment 324 and the septum retainer 218 may be overcome as the needle is withdrawn from the catheter to allow the containment to separate from the hub without undue effort. Alternately, the containment may be held in position by other approaches that minimize forces that might otherwise impede needle withdrawal.

The containment may be connected to the tip protector, according to various example embodiments. As shown in FIGS. 2a and 2b, the containment 324 may be mechanically engaged to the tip protector housing 328. The distal portion of tip protector housing 330 captures a recessed portion of the containment 324 to prevent distal or proximal movement of the containment relative to the tip protector housing. This connection can cause the containment to move with the tip protector both during needle withdrawal and as the catheter introducer is separated from the catheter, helping to assure that any fluids in the lumen of the needle do not escape through the needle notch. The engagement between the tip protector housing and the containment may additionally help position the containment relative to the elastomeric septum of the catheter.

The containment shown in FIGS. 2a and 2b may prevent fluid egress from the notch before the distal end 306 of the needle is moved into the septum 218 during needle withdrawal. After that, the notch 316 may be at least partially open to the ambient environment as shown in FIG. 2b. That is, the containment 324 may receive the notch 316 as the notch moves out of the septum 216, with the containment 324 preventing fluid egress from the notch until the lumen of the needle can no longer receive blood under pressure from within the catheter hub. At this point, risks of blood or other fluid egress from the notch is reduced, due to the lack of exposure to pressure from within the catheter hub that might otherwise push blood through the lumen of the needle and out of the notch.

Figure 3A:
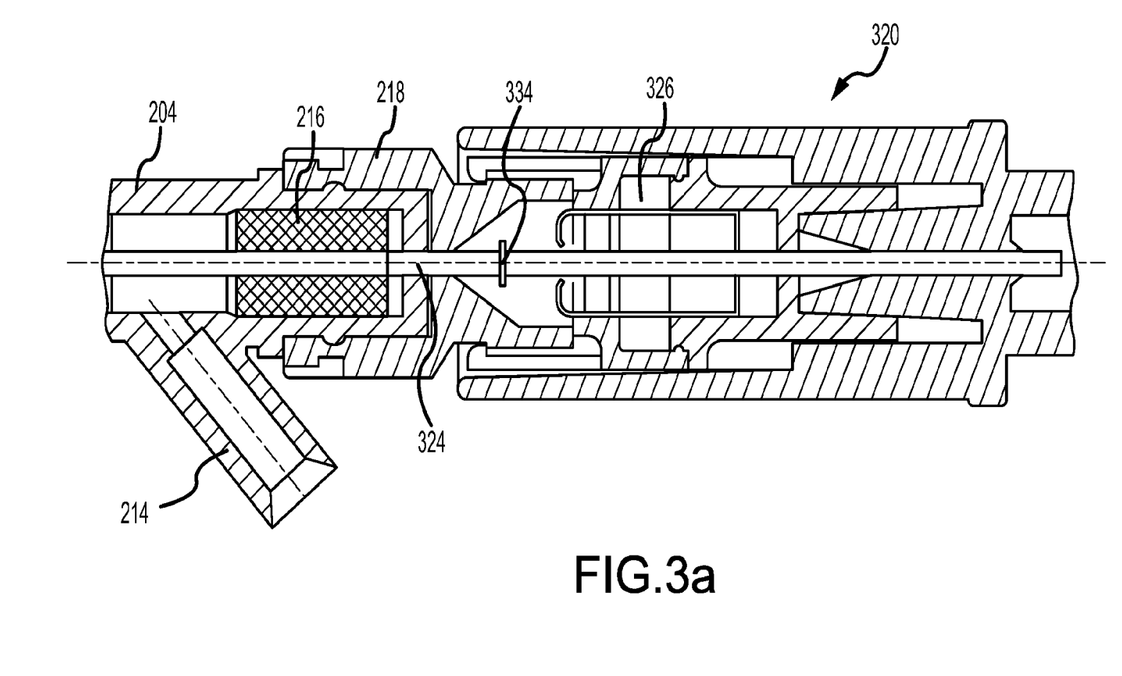
FIG. 3a is a partial, cross sectional view of an intravenous catheter assembly having a notch in the introducer needle and a non-elastomeric containment, according to one example embodiment; the catheter assembly is configured in a ready position.
Figure 3B:
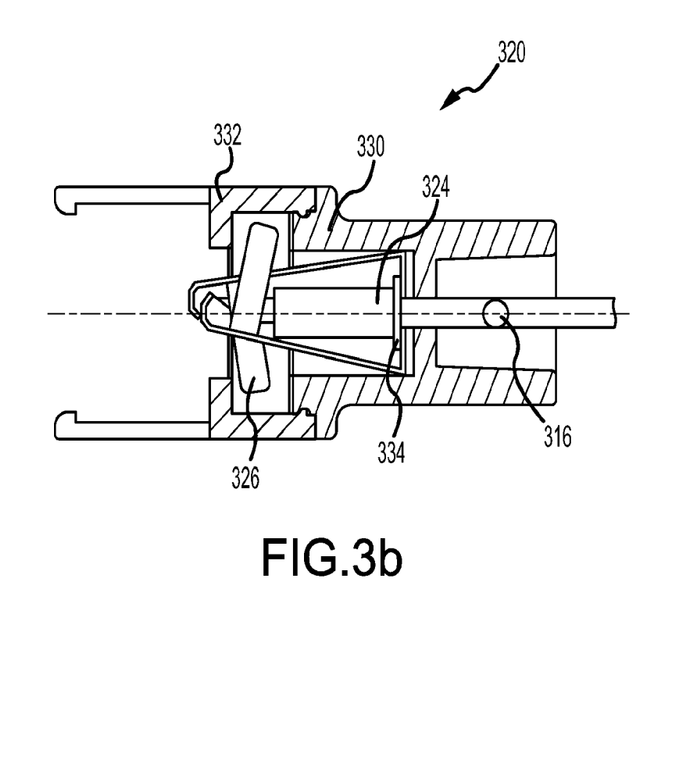
FIG. 3b is a partial, cross sectional view of the intravenous catheter assembly of FIG. 3a, configured in a safe position.

FIGS. 3a and 3b show partial views of another example embodiment of a catheter assembly 200 that includes a containment 324 to prevent the egress of fluids from an introducer needle notch 316. FIG. 3a shows the catheter assembly 100 in a ready position and while 3b shows the safety device 320 of the catheter assembly in a safe position. The containment shown of FIGS. 3a and 3b is constructed of a rigid or semi-rigid material, such as polyurethane, Teflon, or a similar material, rather than an elastomer (i.e., non-elastomeric). As illustrated, the containment 324 includes a tube like structure positioned about the introducer needle 302 in a close fitting arrangement. The proximal end of the containment 324 is connected to a bump washer that interacts with the needle transition 318, as described in greater detail herein. Additionally or alternately, the containment 324 may receive fluids in any space between the containment 324 and introducer needle 302 where the fluids may be contained to prevent blood exposure.

Containments may include features that provide for a close fit with an introducer needle at one or more positions. By way of example, the embodiment of FIGS. 3a and 3b may include a bevel or internal taper at the proximal end to reduce the inner diameter, placing the containment in closer proximity to the introducer needle. The distal end of the containment 324 may additionally include such a bevel or taper, according to some embodiments. The bump washer 334 or clip shown in the embodiment of FIGS. 3a and 3b may, additionally or alternately, urge portions of the containment 324 into closer approximation with the needle to help prevent the egress of blood from a needle notch that is positioned inside of the containment. According to some embodiments, a sealing material that is positioned between the inside of the containment 324 and the needle 302, as the disclosure is not limited to the features shown in FIGS. 3a and 3b.

The catheter hub of FIGS. 3a and 3b includes features that position the containment to receive the notch as the notch emerges from the septum. As shown, the containment is connected to the septum retainer 218 by a slip of slight press fit connection. Alternate embodiments may have the containment positioned inside of a cavity that lies in the septum itself. An interference fit between the containment and cavity in the elastomeric septum may hold the containment in position until the catheter introducer is separated from the catheter after catheter insertion.

The containment of FIGS. 3a and 3b follows movement of the needle transition 318 as the transition is pulled from the catheter hub 204, rather than following the tip protector housing 328 as in the embodiment of FIGS. 2a and 2b. The needle transition 318 contacts and engages the reduced diameter portion of the containment, at the bump washer, as the needle is withdrawn. Further proximal movement of the needle pulls the containment from the catheter. In the illustrated embodiment, the reduced portion of the catheter is defined by a bump washer or clip that is secured to the proximal end of the containment, although the reduced diameter may alternately be formed directly in the tube structure of the containment. The bump washer and containment, when pulled proximally, eventually interact with the tip protector clip to move shift the clip proximally from the ready position to the safe position, where access to the sharp needle tip is prevented.

In the example embodiment of FIGS. 2a and 2b, the notch 316 is positioned distally of the transition 318 and remains positioned internally to the containment 324 after removal from the catheter hub. It is to be appreciated, however, that other configurations are also contemplated. In the embodiment of FIGS. 3a and 3b, the notch 316 is positioned proximally of the transition and emerges from the containment during needle withdrawal. This occurs after the passage of blood into the lumen of the introducer needle is blocked by passage of the distal end of the needle into the septum. As is to be appreciated, this allows the overall length of the septum and even the combined length of the septum and containment, as assembled, to be less than the distance between the distal end of the needle and the proximal end of the notch if the containment follows the notch during needle withdrawal, according to some example embodiments.

Various example embodiments of catheters are described herein for use in accessing the vein of a subject. It is to be appreciated, however, that the example embodiments described herein may alternately be used to access the vasculature of a subject at locations other than a vein, including but not limited to the artery of a subject. It is additionally to be appreciated that the term "clinician" refers to any individual that may be performing a catheter insertion procedure with any of the example embodiments described herein or combinations thereof. Similarly, the term "subject", as used herein, is to be understood to refer to an individual or object in which a catheter is to be inserted, whether human, animal, or inanimate. Various descriptions are made herein, for the sake of convenience, with respect to procedures being performed by a clinician to access the vein of a subject, while the disclosure is not limited in this respect.

It is to be appreciated that the term "notch", as used herein, refers to an opening or passageway that provides a fluid path for blood of a subject to enter the space that lies between catheter and introducer needle of an over the needle type IV catheter assembly. Although the term notch includes an opening in the lateral wall of the introducer needle, other configurations are also to be considered a notch, according to the present disclosure, including configurations that include grooves or slots formed in the lateral wall of the introducer needle that extend under the distal end of the catheter when in the ready position.

It is also to be appreciated that the term "distal", as used herein, refers to the direction, taking along an axis that lies parallel to the needle of a safety catheter assembly that is closest to a subject during catheter insertion. Conversely, the term "proximal", as used herein, refers the direction lying along the axis parallel to the needle that is farther away from the subject when the catheter is inserted into the vein of the subject—that is, opposite to the distal direction.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more features as variously disclosed or otherwise demonstrated herein.

EXAMPLES

The following examples describe details of some of the embodiments disclosed herein. The first example is an intravenous catheter assembly that includes a catheter tube having a proximal end and a distal end. A catheter hub is in fluid communication with the catheter tube and has proximal end, a distal end connected to the proximal end of the catheter tube, and a side port that provides fluid communication to an integrated extension tube. An elastomeric septum is positioned internally to the catheter hub. An introducer that is movable between a ready for use position and a safe position, the introducer includes a needle hub and an introducer needle having a proximal portion connected to the needle hub and distal end having a sharp distal tip, and a tip protector. The introducer needle is disposed, at least in part, within the catheter tube when the introducer needle is in a ready for use position. The tip protector is positioned to prevent access to the sharp distal tip of the introducer needle when in the safe position. The introducer needle defines a lumen that extends from the sharp distal tip toward the proximal portion and includes a notch that is spaced proximal from the sharp distal tip and that provides fluid communication between the lumen of the introducer needle and a flash indication space that lies between the catheter tube and the introducer needle when in the introducer needle is in the ready position. A notch containment is positioned proximal to the elastomeric septum and at least partially external to the catheter hub. The notch containment is constructed and arranged to prevent fluid flow from the notch when the notch of the introducer needle is positioned proximal to the elastomeric septum after the introducer is moved from the ready position.

Example 2 is the intravenous catheter assembly of example 1, wherein the containment separates from the catheter hub when the catheter assembly moves from the ready position to the safe position.

Example 3 is the intravenous catheter assembly of any of the preceding examples, wherein the containment abuts the elastomeric septum when the catheter assembly is in the ready position.

Example 4 is the intravenous catheter assembly of any of the preceding examples, wherein the containment is received by the elastomeric septum when the catheter assembly is in the ready position.

Example 5 is the intravenous catheter assembly of any of the preceding examples, wherein the elastomeric septum and the containment are longer than a distance between sharp distal tip of the introducer needle and a proximal end of the notch when the catheter assembly is in the ready position.

Example 6 is the intravenous catheter assembly of any of the preceding examples, wherein the tip protector includes a tip protector housing and clip that is at least partially housed in the tip protector housing, the containment connected to the tip protector housing.

Example 7 is the intravenous catheter assembly of any of the preceding examples, wherein the containment is connected to the catheter hub or a septum retainer of the catheter hub.

Example 8 is the intravenous catheter assembly of any of the preceding examples, wherein the containment includes an elastomeric material.

Example 9 is the intravenous catheter assembly of any of examples 1-7, wherein the containment includes a tube shaped structure constructed of a non-elastomeric material.

Example 10 is the intravenous catheter assembly of example 9, wherein the tube shaped structure is connected to a needle transition engagement.

What is claimed is:
1. An intravenous catheter assembly having a ready position for use and a safe position, comprising:
    a catheter tube having a proximal end and a distal end;
    a catheter hub having an interior, a proximal end, a distal end connected to the proximal end of the catheter tube so as to be in fluid communication with the catheter tube, and a side port having an opening to the interior to provide fluid communication between an integrated extension tube connected to the side port and the interior of the catheter hub;
    an elastomeric septum secured to the catheter hub proximal to the opening of the side port to prevent fluid leak from the interior of the catheter hub;
    an introducer movable between the ready position and the safe position, the introducer including a needle hub, a tip protector and an introducer needle defined by a wall having an outer surface, a proximal portion connected to the needle hub and a distal end having a sharp distal tip, the introducer needle disposed, at least in part, within the catheter tube when the introducer is in the ready position, the tip protector positioned to prevent access to the sharp distal tip of the introducer needle when the introducer is in the safe position, wherein the introducer needle defines a lumen that extends from the sharp distal tip toward the proximal portion and includes a notch spaced proximal from the sharp distal tip that allows fluid to flow into an annular space between the catheter tube and the introducer needle when the introducer is in the ready position;
    a containment positioned proximal to the elastomeric septum configured to provide a close fit with the needle so as to conform to the surface of the outer wall of the needle along a length at least longer than the notch about the notch when the notch emerges from the septum to prevent the notch from providing an egress for fluid flow after the introducer is moved from the ready position.

2. The intravenous catheter assembly of claim 1, wherein the containment separates from the catheter hub when the introducer moves from the ready position to the safe position.

3. The intravenous catheter assembly of claim 1, wherein the containment abuts the elastomeric septum and is at least partially external of the catheter hub when the catheter assembly is in the ready position.

4. The intravenous catheter assembly of claim 1, wherein the containment is received by the elastomeric septum when the catheter assembly is in the ready position.

5. The intravenous catheter assembly of claim 1, wherein the elastomeric septum and the containment have an overall length longer than the distance between sharp distal tip of the introducer needle and a proximal end of the notch when the catheter assembly is in the ready position.

6. The intravenous catheter assembly of claim 1, wherein the tip protector includes a tip protector housing and a clip that is at least partially housed in the tip protector housing, the containment connected to the tip protector housing.

7. The intravenous catheter assembly of claim 1, wherein the containment is connected to the catheter hub or is held by a septum retainer at the catheter hub.

8. The intravenous catheter assembly of claim 1, wherein the containment includes an elastomeric material.

9. The intravenous catheter assembly of claim 1, wherein the containment is positioned proximal to the septum and at least partially external of the catheter hub to prevent egress of fluid from the notch by conforming about the notch as the introducer needle is withdrawn from the septum and the notch emerges from the septum.

10. The intravenous catheter assembly of claim 1, wherein the containment is held to a housing of the tip protector to prevent movement of the containment relative to the housing.

11. The intravenous catheter assembly of claim 1, wherein the containment includes a tube shaped structure constructed of a non-elastomeric material.

12. The intravenous catheter assembly of claim 11, wherein the tube shaped structure is connected to a needle transition engagement.

13. An intravenous catheter assembly, comprising:
a catheter hub having a body, a proximal end, a distal end having attached thereto a catheter, and an interior defined by the body of the catheter hub in fluid communication with the catheter;
a needle hub having attached to a distal end thereof a needle having a sharp distal tip adapted to extend through the catheter so that the distal tip extends beyond a distal end of the catheter when the catheter assembly is in a ready position for use, the needle forming a lumen having an outer surface therealong and having a notch at a location proximate to the distal tip to provide an egress for fluid flow from the lumen into an annular space formed between an outer wall of the needle and an inner wall of the catheter;
a self sealing septum secured to the interior of the catheter hub to prevent fluid in the interior from leaking out of the catheter hub, the septum providing an access pathway for the needle to enter the interior of the catheter hub and to extend along the catheter;
a containment positioned proximal to the septum configured to provide a close fit with the needle so as to conform to the outer surface of the needle along a length at least longer than the notch about the notch when the notch emerges from the septum to prevent the notch from providing the egress for fluid flow as the needle is being removed from the catheter and the notch emerges from the septum; and
a needle safety device positioned proximal to the containment to prevent access to the distal tip of the needle after the needle is separated from the catheter hub.

14. The catheter assembly of claim 13, wherein the catheter hub includes a side port in open fluid communication with the interior of the catheter hub.

15. The catheter assembly of claim 13, wherein the containment is removably connected to the catheter hub.

16. The catheter assembly of claim 13, wherein the containment is held to a housing of the needle safety device to prevent movement of the containment relative to the housing.

17. The catheter assembly of claim 13, wherein the containment is positioned proximal to the septum and at least partially external of the catheter hub and conforms to the outer wall of the needle about the notch when the notch enters the containment.

18. The catheter assembly of claim 13, wherein the containment being positioned proximally in abutment with the septum to receive the needle and to conform to the outer wall of the needle about the notch as the needle is withdrawn from the septum and the notch emerges from the septum.

* * * * *